(12) United States Patent
Ge et al.

(10) Patent No.: US 10,539,507 B2
(45) Date of Patent: Jan. 21, 2020

(54) ANALYTE DETECTION PACKAGE WITH TUNABLE LENS

(71) Applicant: Hewlett-Packard Development Company, L.P., Houston, TX (US)

(72) Inventors: Ning Ge, Palo Alto, CA (US); Helen A Holder, Palo Alto, CA (US); Anita Rogacs, San Diego, CA (US); Viktor Shkolnikov, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/764,445

(22) PCT Filed: Jan. 29, 2016

(86) PCT No.: PCT/US2016/015765
§ 371 (c)(1),
(2) Date: Mar. 29, 2018

(87) PCT Pub. No.: WO2017/131768
PCT Pub. Date: Aug. 3, 2017

(65) Prior Publication Data
US 2018/0306724 A1    Oct. 25, 2018

(51) Int. Cl.
*G01N 21/65* (2006.01)
*G02B 3/02* (2006.01)
*G03F 7/20* (2006.01)

(52) U.S. Cl.
CPC ............ *G01N 21/658* (2013.01); *G02B 3/02* (2013.01); *G03F 7/2014* (2013.01)

(58) Field of Classification Search
CPC .................................................. G01N 21/658
See application file for complete search history.

(56) References Cited

U.S. PATENT DOCUMENTS

| | | | | |
|---|---|---|---|---|
| 5,255,067 | A | * | 10/1993 | Carrabba ............... G01J 3/44 356/301 |
| 7,450,227 | B2 | | 11/2008 | Dwight et al. |
| 7,561,340 | B2 | | 7/2009 | Tseng et al. |
| 7,738,096 | B2 | | 6/2010 | Zhao et al. |
| 8,599,489 | B2 | | 12/2013 | Shalaev et al. |
| 8,758,985 | B2 | | 6/2014 | Lee et al. |
| 2006/0023209 | A1 | | 2/2006 | Lee et al. |
| 2007/0086001 | A1 | * | 4/2007 | Islam ............... G01N 21/658 356/301 |
| 2007/0086002 | A1 | * | 4/2007 | Islam ............... G01N 21/658 356/301 |

(Continued)

FOREIGN PATENT DOCUMENTS

| WO | WO-2014021808 | | 2/2014 |
|---|---|---|---|
| WO | WO-2015112770 | A1 | 7/2015 |

OTHER PUBLICATIONS

Chen. C. et al; "Tunable Micro-aspherical Lens Manipulated by 2D Electrostatic Forces"; Jun. 5-9, 2005, http://ieeexplore.ieee.org/xpl/articleDetails.jsp?arnumber=1496434&q.

*Primary Examiner* — Shawn Decenzo
(74) *Attorney, Agent, or Firm* — Dicke Billig & Czaja PLLC

(57) ABSTRACT

An analyte detection package includes a chamber, a surface-enhanced luminescence analyte stage within the chamber, and a tunable lens integrated with the package to focus radiation onto the analyte stage.

18 Claims, 6 Drawing Sheets

(56) References Cited

U.S. PATENT DOCUMENTS

| | | | | |
|---|---|---|---|---|
| 2007/0252983 | A1* | 11/2007 | Tong | G01J 3/26 |
| | | | | 356/301 |
| 2009/0147254 | A1* | 6/2009 | Kirby | G01N 21/658 |
| | | | | 356/301 |
| 2011/0267608 | A1* | 11/2011 | Ou | G01N 21/658 |
| | | | | 356/301 |
| 2012/0170050 | A1 | 7/2012 | Savran et al. | |
| 2012/0274935 | A1* | 11/2012 | Yamada | G01N 21/05 |
| | | | | 356/301 |
| 2013/0306838 | A1* | 11/2013 | Matsushita | G02B 26/001 |
| | | | | 250/206 |
| 2014/0211315 | A1* | 7/2014 | Matsushita | G01J 3/26 |
| | | | | 359/578 |
| 2014/0218727 | A1* | 8/2014 | Li | G01N 21/658 |
| | | | | 356/301 |
| 2015/0146180 | A1 | 5/2015 | Lee et al. | |
| 2017/0067831 | A1* | 3/2017 | Yamada | G01N 21/658 |
| 2018/0195966 | A1* | 7/2018 | Ito | G01J 3/4412 |
| 2018/0284028 | A1* | 10/2018 | Ge | G01N 21/658 |
| 2018/0321155 | A1* | 11/2018 | Santori | G01N 21/658 |
| 2019/0003892 | A1* | 1/2019 | Aieta | G02B 21/16 |

* cited by examiner

ANALYTE DETECTION PACKAGE WITH TUNABLE LENS

BACKGROUND

Surface-enhanced luminescence techniques, such as surface-enhanced Raman spectroscopy (SERS), may be used to analyze the structure of inorganic materials or complex organic molecules. Surface-enhanced luminescence techniques focus electromagnetic radiation or light onto an analyte, wherein the radiation scattered by the analyte is detected for analysis.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure.

The present disclosure provides a tunable lens for an analyte detection package. As a tunable lens, a depth of focus of the lens may be controlled or adjusted. More specifically, the lens may be moved relative to an analyte stage of the analyte detection package to "tune" the depth of focus of the lens relative to the stage. In this regard, the depth of focus control may be enhanced.

Figure 1:
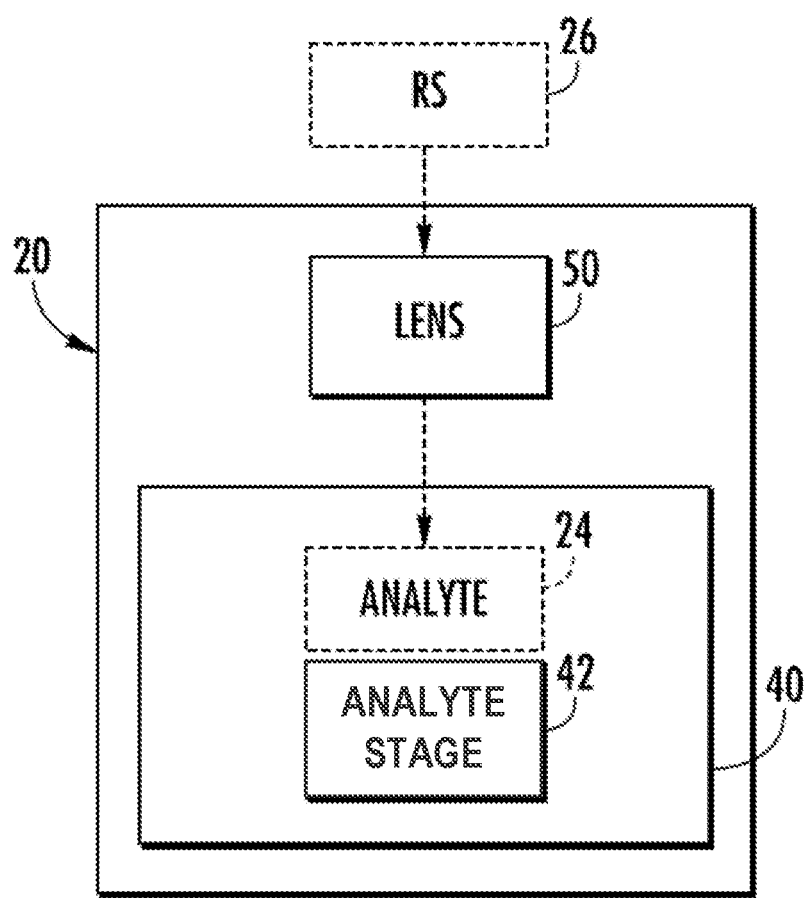
FIG. 1 is a schematic diagram of an example analyte detection package.

FIG. 1 schematically illustrates an example analyte detection package 20. Package 20 comprises a self-contained unit that is to receive and contain an analyte 24 (schematically shown), while radiation from a radiation source 26 (schematically shown) is directed upon or is focused on analyte 24, wherein the radiation scattered or re-emitted by the analyte is detected and analyzed, for example, to identify the structure of inorganic materials or complex organic molecules. In one implementation, package 20 comprises a chamber 40, an analyte stage 42, and a lens 50.

Chamber 40 contains stage 42 and comprises an enclosure forming a defined volume for receiving and containing analyte 24. In one implementation, chamber 40 is formed by a substrate and an opposite or overlying housing which cooperate to form chamber 40. In one implementation, walls of chamber 40 have a metal or metal alloy surface, such as a surface of nickel, gold, platinum, palladium, or rhodium, or alloys thereof.

In one implementation, chamber 40 includes a fill opening through which analyte 24 is deposited into chamber 40. In one implementation, the fill opening is closed by a removable seal that may be peeled away, punctured or torn to expose the fill opening. In one implementation, the fill opening is formed by peeling, puncturing or penetrating through a portion of a wall of chamber 40. In one implementation, a portion of chamber 40 is to be torn away or peeled away to form the fill opening. In another implementation, chamber 40 has a portion which is to be punctured. In another implementation, chamber 40 comprises a septum through which a needle is used to deposit analyte 24 into the interior of chamber 40.

In one implementation, analyte stage 42 comprises a surface-enhanced luminescence analyte stage within chamber 40. A surface-enhanced luminescence (SEL) analyte stage includes any structure or particle that interacts with the deposited analyte so as to enhance the intensity of the radiation scattered or reemitted by the analyte. SEL analyte stage 42 enhances the amount of radiation or the number of photons that are scattered or re-emitted by the analyte upon being impinged by radiation from radiation source 26.

In one implementation, analyte stage 42 comprises an SEL structure or a group of SEL structures within chamber 40 upon which or about which analyte 24 contacts or collects. In one implementation, the SEL structures comprise enhanced fluorescence spectroscopy structures or enhanced luminescence spectroscopy structures.

In one implementation, the SEL structures comprise surface-enhanced Raman spectroscopy (SERS) structures. Such structures may include a metal surface or structure, wherein interactions between the analyte and the metal surface cause an increase in the intensity of the Raman-scattered radiation. Such metal surfaces may include a roughened metal surface or metal islands. In one implementation, such metal islands comprise columnar structures such as pillars, needles, fingers or wires. In some implementations, the columnar structures may include a metal cap or head upon which analyte 24 may be deposited. In one implementation, the SER structures have a nanometer scale to facilitate nano-enhanced Raman spectroscopy (NERS). Such nano-scale NERS structures may increase, for example, by a factor as high as 10^16, the intensity of radiation scattered by the analyte adsorbed on such structures.

In some implementations, the SEL structures are formed from materials and/or are dimensioned so as to bend or flex towards and/or away from one another in response to an applied electric field. In some implementations, the SEL structures are movable and self-actuating such that the structures bend or flex towards one another in response to micro-capillary forces so as to self-organize, wherein such bending facilitates close spacing between the structures for greater scattered radiation intensity.

In another implementation, the SEL structures include SEL particles. Examples of SEL particles include, but are not limited to, electrodes in electrolytic cells and metal colloid solutions.

Lens 50 comprises an optical component to focus the radiation provided by radiation source 26 towards or at stage 42 and onto analyte 24. Lens 50 is integrated as part of package 20 whereby such a lens in radiation system 26 may be omitted. Moreover, because lens 50 is integrated as a part of packaging 20, rather than a part of an external radiation source 26, focus control with lens 50 may be enhanced. In some implementations, the profile of lens 50 may be selected or adjusted for the particular analyte or type of analysis being carried out upon analyte 24. As a result, different packages 20 having different lens profiles may be provided for customized use to analyze different types of analytes. The different profiles of the different lenses 50 may be defined or established during fabrication through adjustment of various process parameters when forming such lenses 50, such as the materials chosen, temperature, time and gravity direction.

As further described below, lens 50 is a tunable lens for the focusing position. As a tunable lens, a depth of focus of lens 50 may be controlled or adjusted. More specifically, lens 50 may be moved relative to stage 42 to "tune" the depth of focus of lens 50 relative to stage 42. In one implementation, the depth of focus control is enhanced from the out-of-focusing error level of a few millimeters to the level of a few micrometers. In one implementation, the depth of focus provided by lens 50, as integrated as part of package 20, is from 1 micrometer to 50 micrometers.

Figure 2:
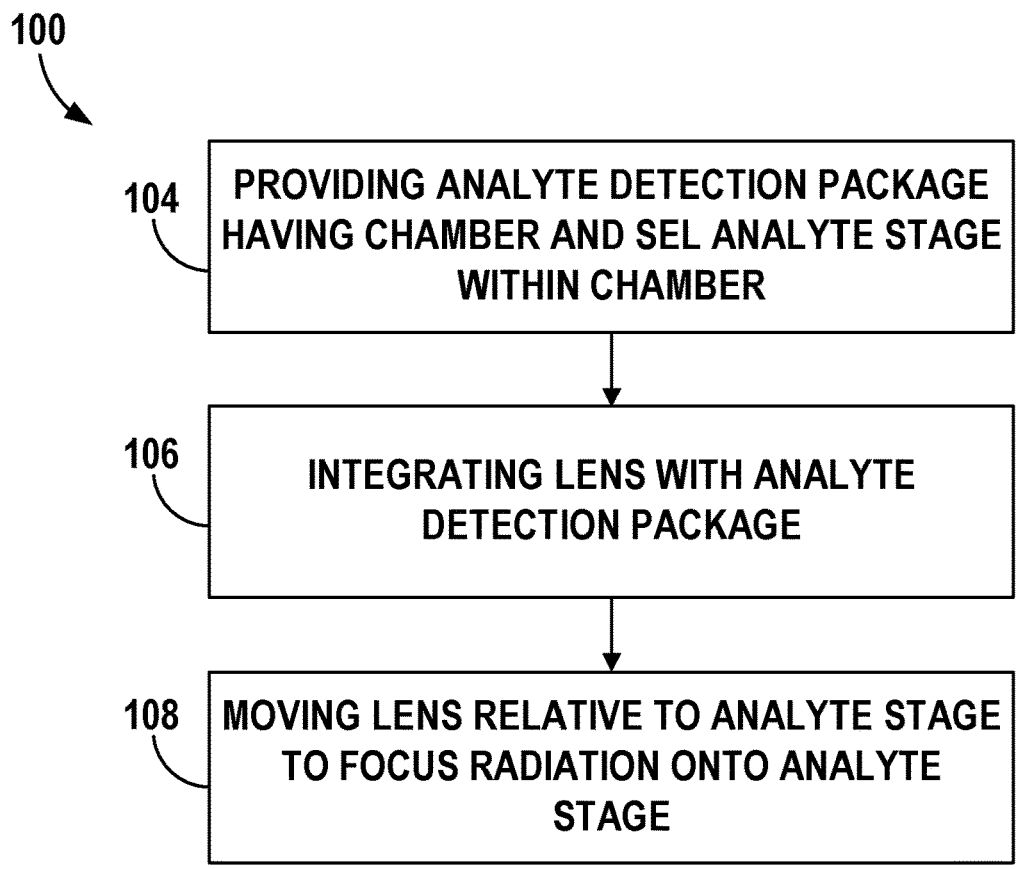
FIG. 2 is a flow diagram of an example method of tuning a lens of an example analyte detection package.

FIG. 2 is a flow diagram outlining an example method 100 of tuning a lens of an analyte detection package, such as lens 50 of package 20. As indicated by block 104, an analyte detection package is formed or otherwise provided, such as package 20. The package has a chamber, and a surface-enhanced luminescence (SEL) analyte stage within the chamber, such as chamber 40 and surface-enhanced luminescence (SEL) analyte stage 42 within chamber 40 of package 20. As indicated by block 106, a lens is integrated with the analyte detection package, such as lens 50 integrated with package 20. In one example, the lens is supported by the package and extends into the chamber, such as lens 50 supported by package 20 and extended into chamber 40. As indicated by block 108, the lens is moved relative to the analyte stage to focus radiation onto the analyte stage, such as lens 50 moved relative to analyte stage 42 to focus radiation onto analyte stage 42.

Figure 3:
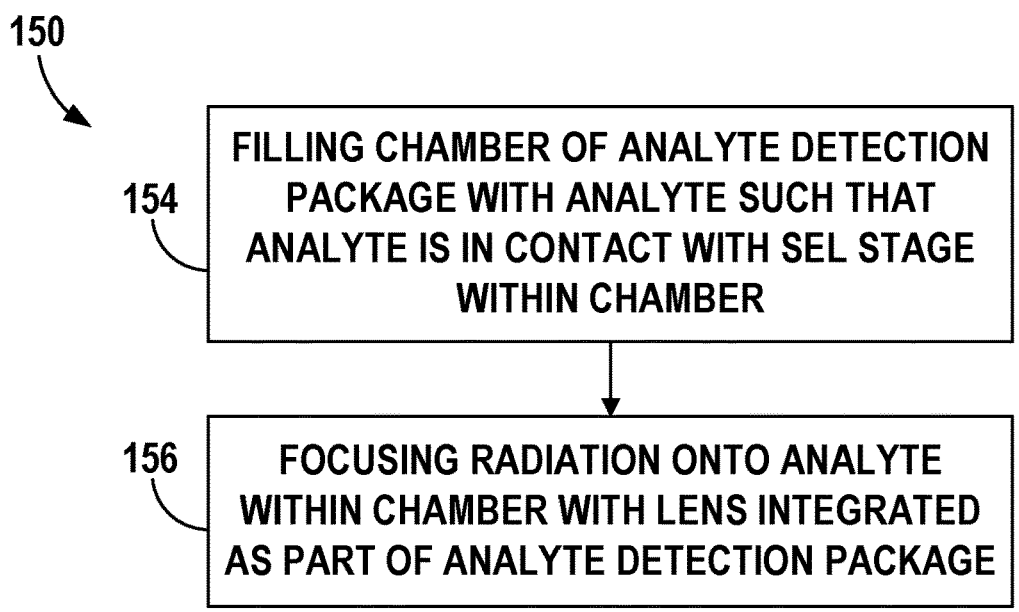
FIG. 3 is a flow diagram of an example method of using an example analyte detection package.

FIG. 3 is a flow diagram outlining an example method 150 of using an analyte detection package when analyzing an analyte, such as package 20 analyzing analyte 24. As indicated by block 154, a chamber of the analyte detection package is filled (partially or fully) with a solution containing the analyte such that the analyte is in contact with an SEL analyte stage within the chamber, such as analyte 24 in contact with analyte stage 42 within chamber 40 of package 20. As indicated by block 156, radiation is focused on to the analyte within the chamber with a lens supported by the analyte detection package, such as radiation of radiation source 26 focused on analyte 24 within chamber 40 by lens 50 of package 20.

The radiation incident upon the analyte, such as analyte 24, may be scattered by the analyte, or may be absorbed and re-emitted by the analyte. As such, the scattered or re-emitted radiation may be sensed and detected. Signals resulting from the sensed or detected radiation may be analyzed to identify or determine characteristics of the analyte. In one implementation, the analyte, such as analyte 24, is dried or is allowed to dry (the liquid carrier of the analyte is evaporated) within the chamber, such as chamber 40, prior to being impinged with the incident radiation focused by the lens, such as lens 50.

Figure 4:
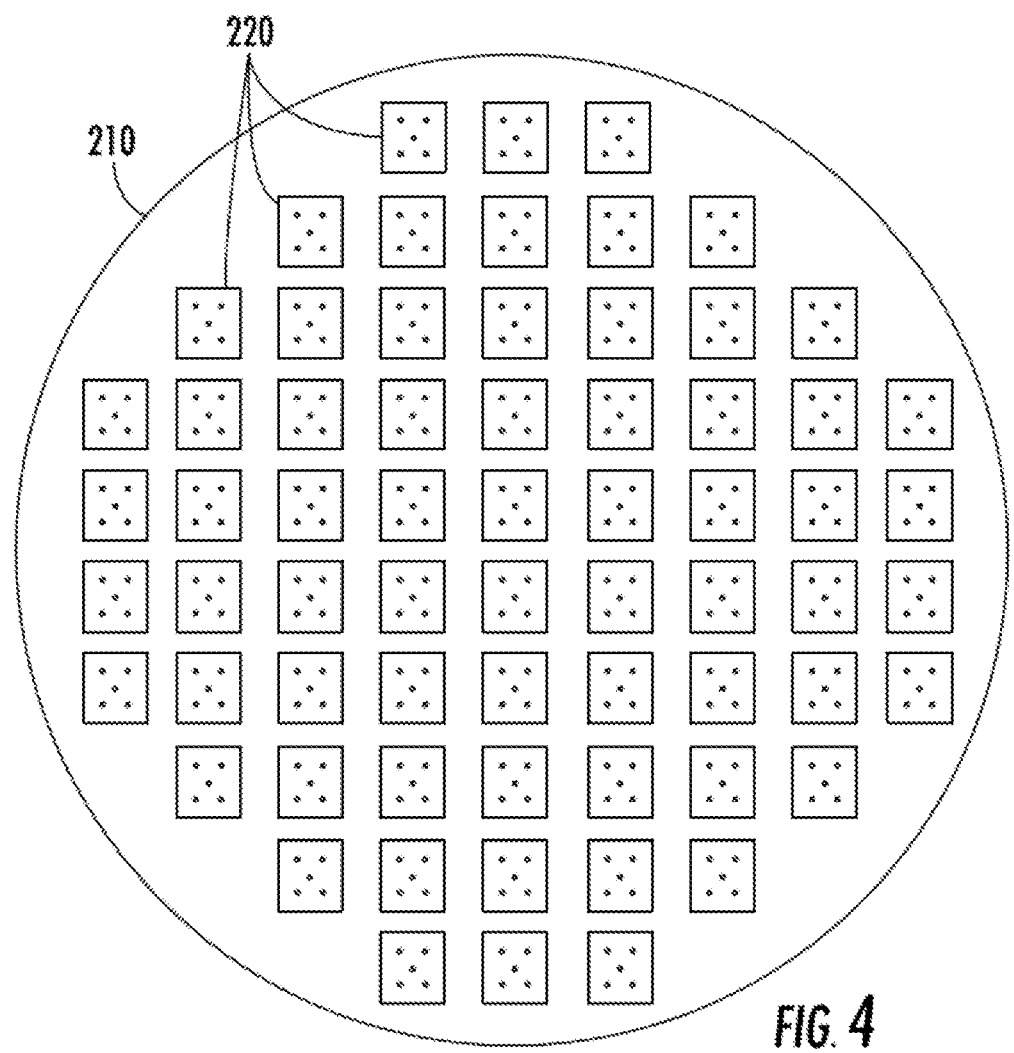
FIG. 4 is an example wafer including an array of example analyte detection packages.
Figure 5:
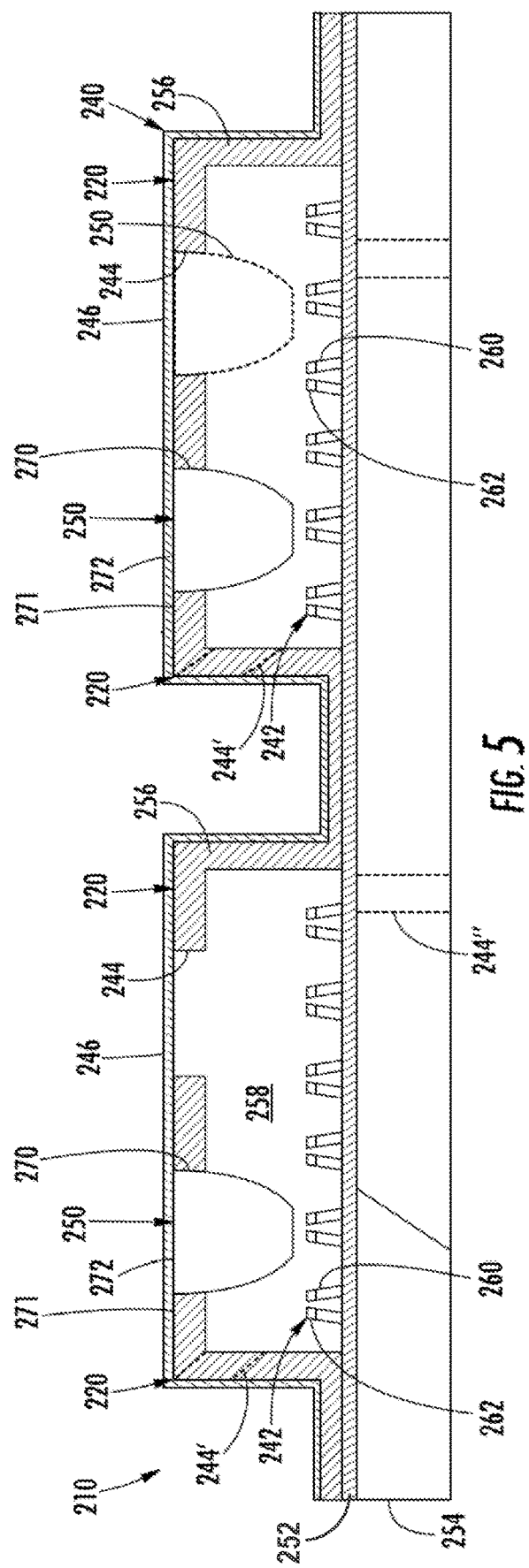
FIG. 5 is a sectional view illustrating example analyte detection packages of the wafer of FIG. 4.

FIGS. 4 and 5 illustrate multiple analyte detection packages 220, as example implementations of analyte detection package 20. As schematically illustrated in the example of FIG. 4, packages 220 may be formed using semiconductor integrated circuit fabrication techniques as part of a wafer 210. The individual packages 220, formed as part of the wafer 210, are then subsequently separated into individual packages or individual sets of packages.

FIG. 5 is a sectional view schematically illustrating two example packages 220 formed as part of wafer 210. As illustrated in FIG. 5, each package 220 includes a chamber 240, a surface-enhanced luminescence analyte stage 242, a fill opening 244, a seal 246, and a lens 250. Similar to chamber 40, chamber 240 contains stage 242 and comprises a defined volume for receiving and containing analyte 24 (FIG. 1). In the example illustrated, chamber 240 is formed or defined by or between a base or substrate 254 and an enclosure or housing 256. Substrate 254 serves as a platform upon which stage 242 is formed, and may be made from any suitable material such as silicon, glass, plastic, paper, polydimethylsiloxane, a transparent material, rubber and/or a membrane, for example.

In one implementation, stage 242 is formed on a layer 252, as supported by substrate 254. Layer 252 comprises a thin-film layer or a layer of a thin-film structure on substrate 254. In one implementation, layer 252 comprises an inter layer dielectric, and may be formed of silicon dioxide (e.g., tetraethoxysilane (TEOS)), silicon nitride, silicon carbide, hafnium oxide or other suitable material or combination of such materials. In other implementations, layer 252 may be a thin-film metal, for example, Au, Ta or other suitable material.

In one implementation, substrate 254 supports housing 256 such that housing 256 extends from substrate 254. In the example illustrated, portions of layer 252 are positioned between substrate 254 and housing 256. In other implementations, housing 256 may contact and directly extend from substrate 254.

Housing 256 cooperates with substrate 254 to form and define an interior 258 of chamber 240. Housing 256 protects stage 242 from exposure to the environment and may reduce or prevent oxidation of surfaces of stage 242 prior to use. Additionally, housing 256 may reduce or prevent unintentional or premature exposure of stage 242 to extraneous substances or an analyte that stage 242 is intended to detect. Although housing 256 and substrate 254 are illustrated as forming a rectangular shaped interior 258, interior 258 may have other shapes in other implementations.

In one implementation, housing 256 comprises an orifice plate and includes walls that are formed by selectively plating a mandrel with a layer or layers of metal and subsequently removing the mandrel to form the housing with apertures. In one implementation, housing 256 has a metal surface such as nickel, gold, platinum or rhodium, for example. In one implementation, the walls of housing 256 are formed entirely from such a metal. In other implementations, housing 256 may be formed from non-metallic materials using processes other than plating.

Stage 242 comprises a surface-enhanced luminescence (SEL) analyte stage within chamber 240, and includes structures 260 that interact with the deposited analyte so as to enhance the intensity of the radiation scattered or re-emitted by the analyte. Such structures enhance the amount of radiation or the number of photons that are scattered or re-emitted by the analyte upon being impinged by radiation from a radiation source.

In the example illustrated, structures 260 comprise columnar structures, such as pillars, needles, wires or fingers. In the example illustrated, each of the structures 260 include a metal cap or head 262 upon which analyte may be deposited. In some implementations, structures 260 are formed from materials and/or are dimensioned so as to bend or flex towards and/or away from one another in response to an applied electric field or in response to micro-capillary forces so as to self-organize, wherein such bending facilitates close spacing between the structures for greater scattered radiation intensity. In one implementation, structures 260 have a nanometer scale to facilitate nano-enhanced Raman spectroscopy (NERS). Such nano-scale NERS structures may increase, for example, by a factor as high as 10-16, the intensity of radiation scattered by the analyte absorbed on such structures.

In other implementations, stage 242 comprises other SEL structures such as enhanced fluorescence spectroscopy structures or enhanced luminescence spectroscopy structures. In other implementations, stage 242 comprises particles, such as nanoparticles, that interact with the deposited analyte to enhance the intensity of the radiation scattered by the analyte. Examples of such particles include electrodes in electrolytic cells or metal colloid solutions.

Fill opening 244 comprises a passage extending from the exterior of package 220 to interior 258 of chamber 240. In one implementation, fill opening 244 is sized and located to facilitate filling of interior 258 with the analyte to be tested. In the example illustrated, fill opening 244 extends through housing 256. In other implementations, and as indicated by broken lines, package 220 may additionally or otherwise include other fill openings such as fill opening 244' extending through a side of housing 256 or fill opening 244" extending through substrate 254.

Seal 246 comprises a panel or layer of material coupled or secured to package 220 across or over fill opening 244 so as to cover or close fill opening 244. In one implementation, seal 246 provides a hermetic seal to inhibit contamination of interior 258. For example, seal 246 inhibits oxidation of the metal surfaces within interior 258 prior to use of package 220. Seal 246 further indicates previous use of package 220. Seal 246 may be formed from a polymer tape, plastic, transparent material, plastic sheeting, foil material, foil sheeting, film, membrane, wax or polydimethylsiloxane, for example.

When analyte is to be deposited within interior 258, seal 246 may be altered to provide access through fill opening 244. In one implementation, seal 246 is releasably or removably adhered to housing 256, for example, by pressure sensitive adhesive that allows seal 246 to be peeled away from fill opening 244. In another implementation, seal 246 is formed from a material and/or is dimensioned so as to be punctured through fill opening 244 and/or torn away from fill opening 244. In other implementations, seal 246 comprises a septum that allows insertion of a needle through fill opening 244, wherein the septum resiliently closes upon withdrawal of the needle. In other implementations, seal 246 is provided by a lid, top, door, hatch or cap that temporarily seals or closes fill opening 244. In some implementations, seal 246 is omitted.

Lens 250 comprises an optical component supported by housing 256 opposite to stage 242 so as to focus incident radiation onto portions of stage 242. In the example illustrated, lens 250 comprises a convex lens. In the example illustrated, lens 250 extends through and fills a bore or aperture 270 extending through housing 256. In one implementation, lens 250 has an upper surface 272 inset within or flush with the outer surface 271 of housing 256, facilitating the covering of surface 272 with a membrane or film of seal 246 to protect the surface of lens 250 prior to use of lens 250.

Lens 250 projects from aperture 270 into interior 258 into close proximity with stage 242. As a result, lens 250 may have enhanced focusing control depth as close as 1 micrometer to 50 micrometers with respect to analyte supported by stage 242. Because lens 250 is provided on package 220, depth of focus for distance control may be automatically provided by package 220, where such control is more precise due to greater manufacturing control and reduced manufacturing tolerances associated with package 220. In one implementation, and as described below, lens 250 is a tunable lens such that a depth of focus of lens 50 may be varied or controlled.

In some implementations, and as indicated by broken lines, package 220 may support a plurality of lenses 250. In one implementation, each of the plurality of lenses 250 focuses incident radiation towards respective portions of stage 242 and the contained analyte. In such implementations, one of the other fill openings 244', 244" are provided. Although two of such lenses 250 are shown, package 220 may support a different number of lenses 250 in other implementations.

Figure 6:
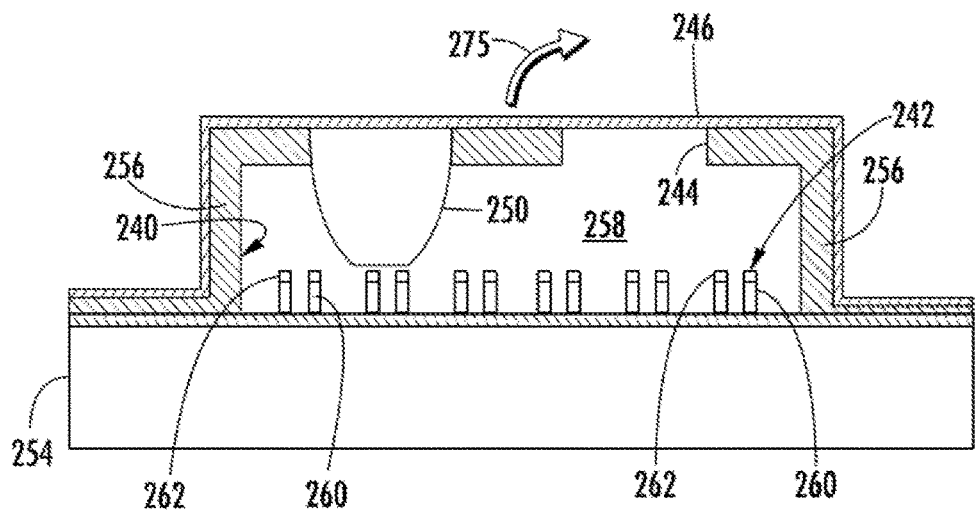
FIGS. 6, 7, and 8 are schematic sectional views illustrating an example method of using an example analyte detection package of FIG. 5.
Figure 7:
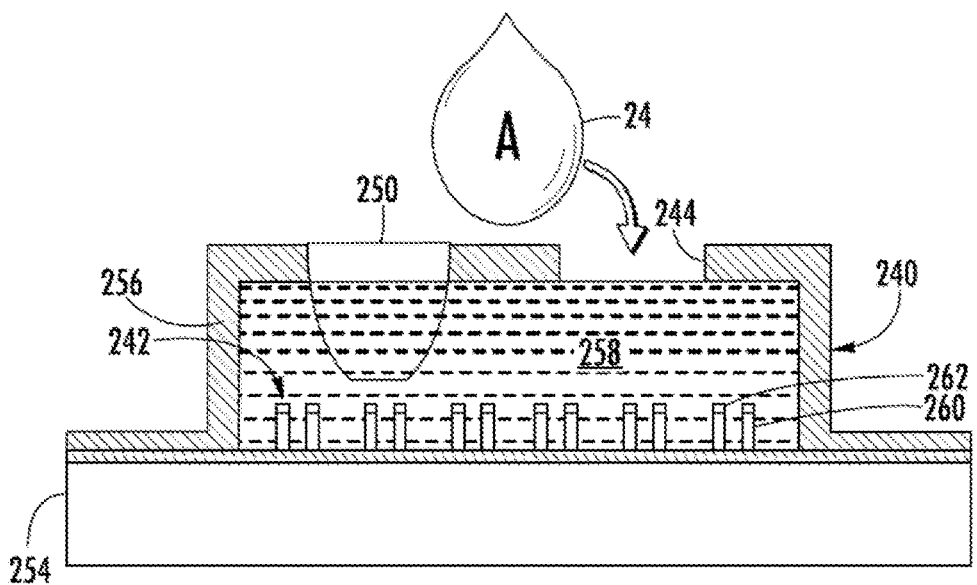
Figure 8:
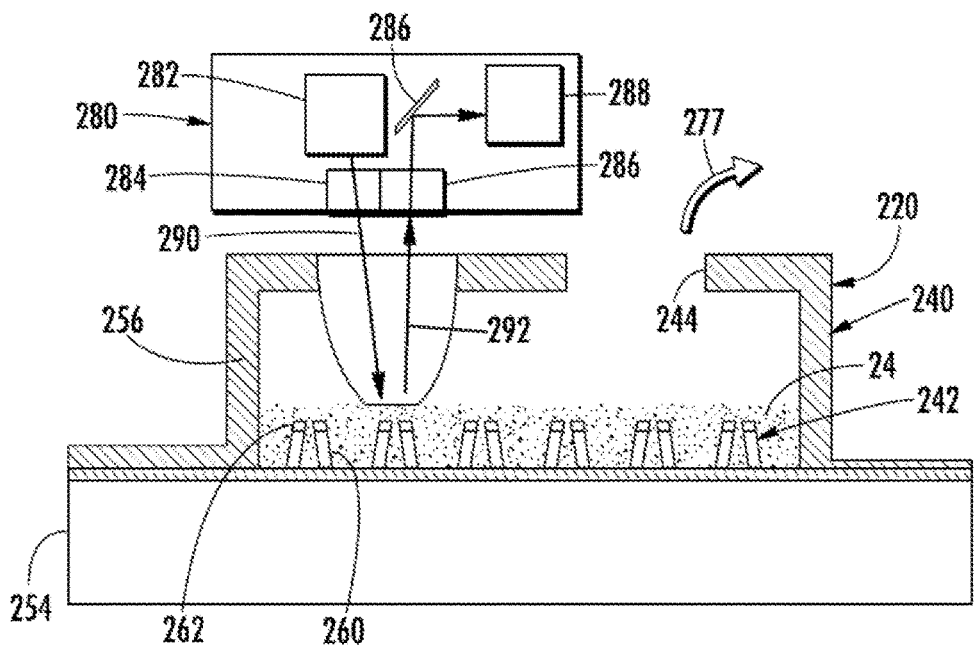

FIGS. 6, 7, and 8 illustrate one example of use of package 220. As illustrated in the example of FIG. 6, seal 246 is peeled away from housing 256, as indicated by arrow 275, and as illustrated in the example of FIG. 7, analyte 24 is deposited into interior 258 through fill opening 244.

As illustrated in FIG. 8, analyte 24 is dried, or allowed to dry or evaporate, as indicated by arrow 277. As further illustrated in FIG. 8, package 220 is presented to a reading device or reader 280 which, in one implementation, comprises a radiation emitter 282, focusing optics 284, receiving optics 286, and a detector 288. Radiation emitter 282 emits photons 290 which are directed by optics 284 onto lens 250, and lens 250 focuses the radiation onto stage 242 and analyte 24. The directed photons 290 are scattered by analyte 24, wherein the intensity of the scattered photons or radiation is enhanced by stage 242. The scattered photons 292 return to reader 280, where optics 286, in the form of a lens and/or mirror arrangement, direct the scattered photons 292 to detector 288 which outputs signals based upon the detected photons. In one implementation, a processor, following instructions in a non-transitory computer-readable medium, receives the signals and analyzes the signals to identify or determine characteristics of analyte 24. In one implementation, radiation emitter 282 comprises a laser, wherein optics 284 comprises a convex lens or other optical component or components which impinge lens 250 with a column laser beam.

Figure 9:
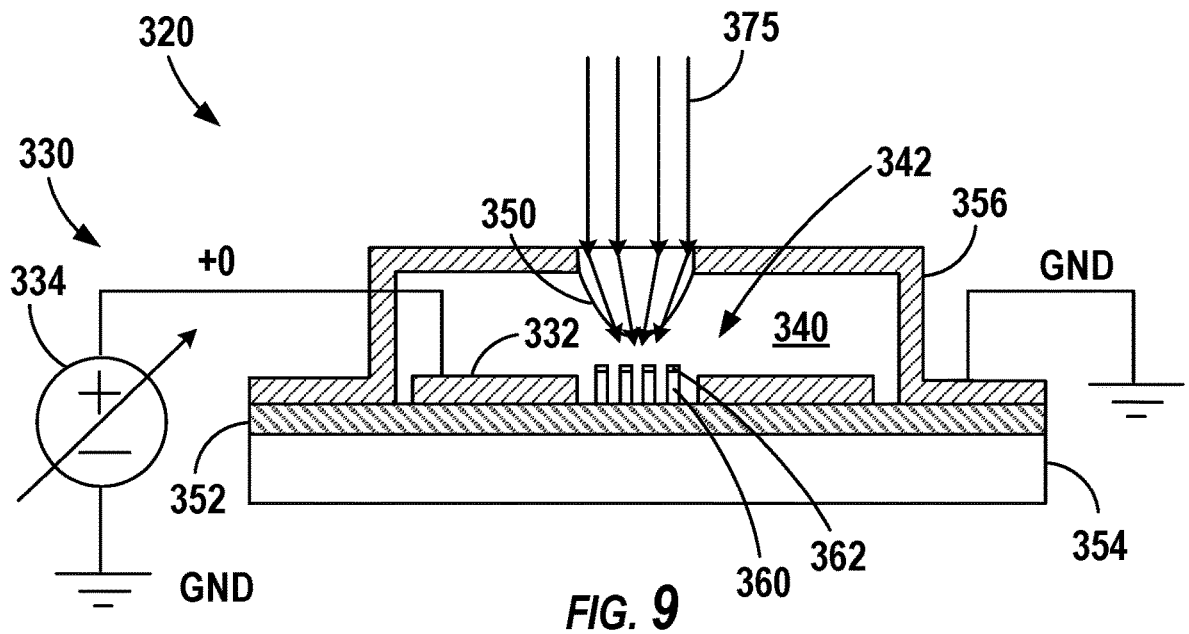
FIGS. 9 and 10 are schematic sectional views illustrating an example analyte detection package with a tunable lens.
Figure 10:
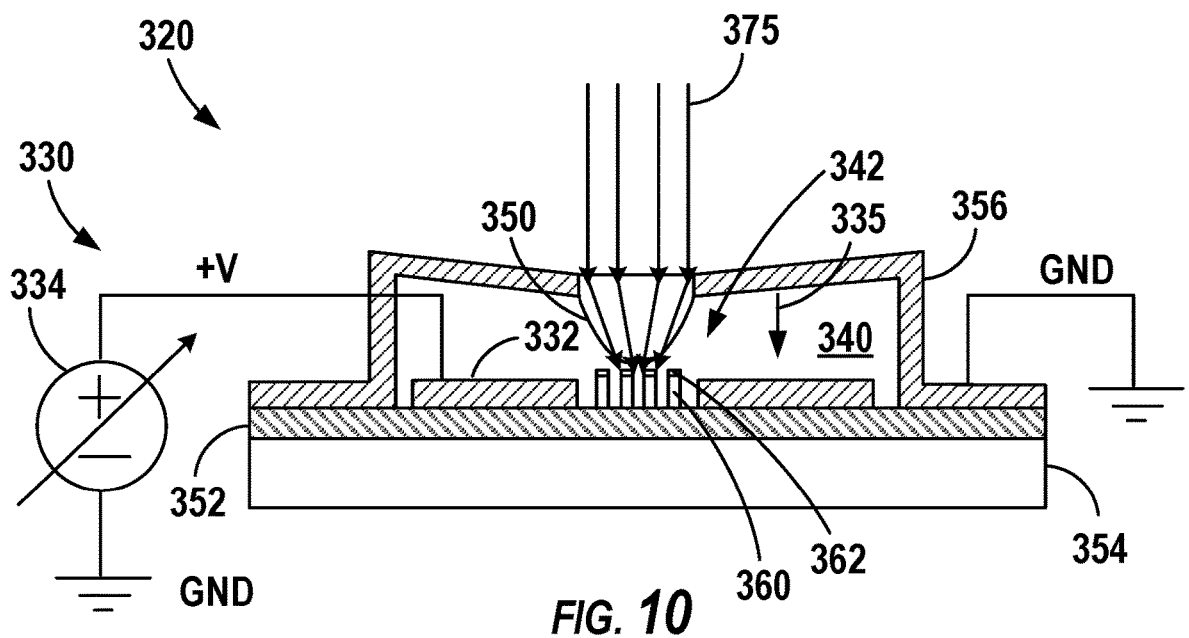

FIGS. 9 and 10 illustrate an analyte detection package 320, as an example implementation of package 220 and package 20, with a tunable lens 350, as an example implementation of lens 250 and lens 50. As schematically illustrated in the example of FIG. 9, package 320 includes a chamber 340, a surface-enhanced luminescence (SEL) analyte stage 342, and lens 350.

Similar to chamber 240 and chamber 40, chamber 340 contains analyte stage 342 and comprises an enclosure forming a defined volume for receiving and containing analyte 24 (FIG. 1). In one implementation, chamber 340 is formed or defined by or between a base or substrate 354 and an enclosure or housing 356.

Similar to stage 242, stage 342 is formed on a layer 352, as supported by substrate 354. Layer 352 comprises a thin-film layer or a layer of a thin-film structure on substrate 354. In one implementation, layer 352 comprises an inter layer dielectric, and may be formed of silicon dioxide (e.g., tetraethoxysilane (TEOS)), silicon nitride, silicon carbide, hafnium oxide or other suitable material or combination of such materials. In other implementations, layer 352 may be a thin-film metal, for example, Au, Ta or other suitable material.

Similar to stage 242 and stage 42, stage 342 includes SEL structures 360 that interact with the deposited analyte to enhance the intensity of the radiation scattered or re-emitted by the analyte. In the example illustrated, structures 360 include columnar structures, such as pillars, needles, wires or fingers. In the example illustrated, each of the structures 360 include a metal cap or head 362 upon which analyte may be deposited.

Lens 350 is a tunable lens. As a tunable lens, a depth of focus of lens 350 may be controlled or "tuned". More specifically, and as schematically illustrated in the example of FIG. 10, lens 350 may be moved relative to stage 342 to vary or adjust (i.e., tune) the depth of focus of lens 350 relative to the SEL structures of stage 342. In one implementation, the depth of focus control is enhanced from the level of a few millimeters to the level of a few micrometers. In one implementation, the depth of focus provided by lens 350, as integrated with package 320, is from 1 micrometer to 50 micrometers.

To adjust a depth of focus and "tune" lens 350, package 320 includes an actuator 330. Actuator 330 comprises a system, element or components, which move lens 350 relative to stage 342 to change or control a depth of focus of lens 350. Example implementations of actuator 330 include an electrostatic actuator, piezoelectric actuator, electromagnetic actuator, pneumatic actuator, thermal bimorph actuator, and a shape memory alloy actuator. In one implementation, actuator 330 comprises a micro-electro-mechanical system (MEMS) actuator.

In the example illustrated in FIGS. 9 and 10, actuator 330 is an electrostatic (or capacitive) actuator. As an electrostatic actuator, operation of actuator 330 is based on the attraction (and repulsion) of electric charge through electrostatic force (attraction) between two elements or plates including, for example, a movable or moving element or plate, and a fixed, stationary or static element or plate. Example electrostatic actuators include a comb-drive actuator, and a parallel plate actuator.

In one implementation, housing 356, including at least a portion of housing 356 supporting lens 350, is conductive and comprises the moveable "plate" of actuator 330, and substrate 354, with analyte stage 342 formed or supported thereon, comprises the fixed or static "plate" of actuator 330 such that housing 356, including at least a portion of housing 356 supporting lens 350, is selectively moved relative to substrate 354, as indicated by arrow 335.

In one implementation, actuator 330 includes a conductive layer 332 formed on or supported by substrate 354. Conductive layer 332 is connected to a power supply 334 such that an applied voltage (+V) causes movement (deflection) of housing 356 toward substrate 354, including, more specifically, movement (deflection) of at least a portion of housing 356 supporting lens 350 toward substrate 354. As lens 350 is integrated with housing 356, lens 350 moves toward substrate 354, including, more specifically, toward analyte stage 342, with movement of housing 356.

In one implementation, power supply 334 is a variable or adjustable voltage control or source such that an amount of movement (deflection) of housing 356, and a corresponding movement of lens 350, may be varied. As such, a depth of focus of lens 350 may be a controlled or "tuned" with varying voltage. Thus, radiation, as indicated by arrows 375, provided by a radiation source, such as radiation source 26 (FIG. 1), may be focused on stage 42 including, more specifically, SEL structures of stage 42.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. An analyte detection package, comprising:
a chamber;
a surface-enhanced luminescence analyte stage within the chamber;
a tunable lens integrated with the package to focus radiation generated externally of the package onto the analyte stage;
a housing to support the lens; and
an actuator to move a portion of the housing supporting the lens to move the lens relative to the analyte stage,
wherein the portion of the housing supporting the lens forms a portion of a wall of the chamber.

2. The analyte detection package of claim 1, the lens to move relative to the analyte stage to adjust the focus of the lens.

3. The analyte detection package of claim 1, further comprising:
a substrate to support the analyte stage;
the housing extended from the substrate to form the chamber therebetween; and
the actuator to move the lens relative to the substrate to adjust the focus of the lens.

4. The analyte detection package of claim 3, the actuator to move the portion of the housing supporting the lens relative to the substrate to move the lens relative to the analyte stage.

5. The analyte detection package of claim 3, the lens extended through an aperture of the housing into an interior of the chamber.

6. The analyte detection package of claim 1, the actuator to variably move the lens toward the analyte stage.

7. The analyte detection package of claim 1, wherein the actuator comprises a micro-electro-mechanical system actuator.

8. The analyte detection package of claim 1, wherein the surface-enhanced luminescence analyte stage includes surface-enhanced Raman spectroscopy structures.

9. An analyte detection package, comprising:
a surface-enhanced luminescence analyte stage;
a lens to focus radiation onto the analyte stage;
a housing supporting the lens;
a substrate supporting the analyte stage and the housing; and
an actuator to move the lens relative to the substrate to adjust a focus of the lens,
wherein the lens extends through an aperture of the housing.

10. The analyte detection package of claim 9, the actuator to move a portion of the housing supporting the lens relative to the substrate to adjust the focus of the lens.

11. The analyte detection package of claim 10, wherein the actuator comprises an electrostatic actuator, and wherein the portion of the housing supporting the lens is conductive and comprises a moveable element of the electrostatic actuator.

12. The analyte detection package of claim 9, the lens to focus radiation onto the analyte stage from a radiation source external to the package.

13. A method of tuning a lens of an analyte detection package, comprising:
providing an analyte detection package having a chamber and a surface-enhanced luminescence analyte stage within the chamber;

integrating a lens with the analyte detection package, including supporting the lens with a housing and extending the lens through an aperture of the housing and into an interior of the chamber; and moving the lens relative to the analyte stage to focus radiation from a radiation source external to the analyte detection package onto the analyte stage.

14. The method of claim 13, wherein moving the lens includes variably adjusting the focus of the lens.

15. The method of claim 13, wherein providing the analyte detection package and integrating the lens with the analyte detection package comprises:

supporting the housing and the analyte stage with a substrate; and defining the chamber between the housing and the substrate.

16. The method of claim 15, wherein moving the lens includes moving a portion of the housing supporting the lens relative to the substrate.

17. The method of claim 13, wherein moving the lens includes moving the lens with a micro-electro-mechanical system actuator.

18. The method of claim 13, wherein the surface-enhanced luminescence analyte stage includes surface-enhanced Raman spectroscopy structures.

* * * * *